United States Patent
Fukudome et al.

(10) Patent No.: US 8,940,845 B2
(45) Date of Patent: Jan. 27, 2015

(54) METHOD FOR PRODUCING WATER-ABSORBING RESIN

(75) Inventors: Shinya Fukudome, Himeji (JP); Tetsuhiro Hinayama, Himeji (JP); Noriko Honda, Kakogawa (JP); Junichi Takatori, Himeji (JP)

(73) Assignee: Sumitomo Seika Chemicals Co., Ltd., Hyogo (JP)

(*) Notice: Subject to any disclaimer, the term of this patent is extended or adjusted under 35 U.S.C. 154(b) by 0 days.

(21) Appl. No.: 14/111,249

(22) PCT Filed: Apr. 19, 2012

(86) PCT No.: PCT/JP2012/060629
§ 371 (c)(1),
(2), (4) Date: Oct. 11, 2013

(87) PCT Pub. No.: WO2012/144566
PCT Pub. Date: Oct. 26, 2012

(65) Prior Publication Data
US 2014/0031507 A1    Jan. 30, 2014

(30) Foreign Application Priority Data

Apr. 21, 2011  (JP) .................................. 2011-095344

(51) Int. Cl.
*C08F 2/00*   (2006.01)
*C08F 4/04*   (2006.01)
(Continued)

(52) U.S. Cl.
CPC ................. *B01J 20/261* (2013.01); *C08F 2/32* (2013.01); *A61L 15/22* (2013.01); *A61L 15/60* (2013.01);
(Continued)

(58) Field of Classification Search
CPC .......... C08F 2/32; C08F 120/06; B01J 20/261

USPC .................................. 526/215, 219.3, 317.1
See application file for complete search history.

(56) References Cited

U.S. PATENT DOCUMENTS 5,180,798 A * 1/1993 Nakamura et al. .............. 526/66
5,185,413 A    2/1993 Yoshinaga

FOREIGN PATENT DOCUMENTS

CN    1788022 A    6/2006
EP    0 398 653 A1    11/1990
(Continued)

OTHER PUBLICATIONS

International Search Report for International Application No. PCT/JP2012/060629 dated Jul. 24, 2012.
Supplementary European Search Report dated Sep. 8, 2014 in the corresponding European Patent Application No. 12774778.0.

*Primary Examiner* — William Cheung
(74) *Attorney, Agent, or Firm* — Kratz, Quintos & Hanson, LLP (57) ABSTRACT

The invention provides a novel method for producing a water-absorbent resin comprising: subjecting at least one water-soluble ethylenic unsaturated monomer to reversed-phase suspension polymerization in a petroleum hydrocarbon dispersion medium, the reversed-phase suspension polymerization being conducted using a 0.00005 to 0.00016 mole of water-soluble azo initiator for radical polymerization per mole of the water-soluble ethylenic unsaturated monomer in the presence of 0.000015 to 0.00015 mole of hypophosphorous compound per mole of the water-soluble ethylenic unsaturated monomer. According to the method, the environmental impact can be lessened by reducing the amount of petroleum hydrocarbon dispersion medium released to the outside of the system, and the method makes it possible to obtain a water-absorbent resin having a high water-retention capacity and water-absorption capacity under a load, and a small content of water soluble component at the same time.

7 Claims, 1 Drawing Sheet

(51) Int. Cl.
  *C08F 20/06* (2006.01)
  *B01J 20/26* (2006.01)
  *C08F 2/32* (2006.01)
  *A61L 15/22* (2006.01)
  *A61L 15/60* (2006.01)
  *C08J 3/24* (2006.01)
  *C08K 3/32* (2006.01)
  *C08L 33/02* (2006.01)
  *C08F 120/06* (2006.01)

(52) U.S. Cl.
  CPC . *C08J 3/245* (2013.01); *C08K 3/32* (2013.01); *C08L 33/02* (2013.01); *C08F 120/06* (2013.01); *C08F 4/04* (2013.01)
  USPC ............... 526/215; 526/219.3; 526/317.1

(56) References Cited

FOREIGN PATENT DOCUMENTS

| | | |
|---|---|---|
| EP | 1 714 985 A1 | 10/2006 |
| JP | H02-300210 | 12/1990 |
| JP | H03-227301 | 10/1991 |
| JP | H04-279606 | 10/1992 |
| JP | H04-292603 | 10/1992 |
| JP | H04-331205 | 11/1992 |
| JP | H06-145253 | 5/1994 |
| JP | H06-287233 | 10/1994 |
| JP | H06-345819 | 12/1994 |
| JP | H08-120018 | 5/1996 |
| JP | H11-29605 | 2/1999 |
| JP | 2001-40014 | 2/2001 |
| JP | 2006-176570 A1 | 7/2006 |
| JP | 2010-158667 A1 | 7/2010 |

* cited by examiner

US 8,940,845 B2

METHOD FOR PRODUCING WATER-ABSORBING RESIN

This patent application is a U.S. national stage entry under 35 U.S.C. Section 371 of International Patent Application No. PCT/JP2012/060629 filed on Apr. 19, 2012, which claims the benefit of foreign priority to Japanese Patent Application No. 2011-095344 filed Apr. 21, 2011, the disclosures of all of which are hereby incorporated by reference in their entireties.

TECHNICAL FIELD

The present invention relates to a method for producing a water-absorbent resin, and a water-absorbent resin obtained by the method. More specifically, the invention relates to a method for producing a water-absorbent resin using reversed-phase suspension polymerization, the method being environmentally friendly by reducing the amount of petroleum hydrocarbon dispersion medium released to the outside of the reaction system, and the method being able to produce a water-absorbent resin having a high water-retention capacity and water-absorption capacity under a load, and a small amount of water soluble component. The invention also relates to a water-absorbent resin obtained by this method.

BACKGROUND ART

In recent years, water-absorbent resin has been widely used in various fields, including hygienic materials, such as disposable diapers and sanitary napkins, agricultural and horticultural materials, such as water-retaining agents and soil conditioners, and industrial materials, such as water-blocking agents and agents for preventing dew condensation. Of these, water-absorbent resin is frequently used in, in particular, hygienic materials, such as disposable diapers and sanitary napkins.

As the water-absorbent resin, for example, hydrolysates of starch-acrylonitrile graft copolymers, neutralized products of starch-acrylate graft copolymers, saponified products of vinyl acetate-acrylic ester copolymers, and crosslinked products of partially neutralized acrylic acid polymers are known.

The water-absorbent resin is mainly produced by subjecting a water-soluble ethylenic unsaturated monomer to reversed-phase suspension polymerization or aqueous solution polymerization. Of these methods, the reversed-phase suspension polymerization uses an organic solvent as a dispersion medium. Therefore, the environmental impact, such as the emission of organic solvent to the outside of the system, e.g., to the air, must be taken into consideration. Further, for example, provision of an organic solvent recovery system is required to prevent organic solvent emissions caused by the high heat of polymerization or a rapid reaction.

Further, in hygienic materials, such as disposable diapers, the water-absorbent resin is required to have, as a desirable property, a high water-absorption capacity under a load to reduce the amount of re-wetting when pressure is applied after the absorption of a fluid, in addition to having a high water-retention capacity. Further, having a small amount of water soluble component is also an important requirement for preventing a viscous fluid from sticking to the skin. However, it is difficult for known methods for producing a water-absorbent resin to sufficiently achieve a balance among these properties.

In particular, in terms of a water-absorbent resin, the water-retention capacity and the water-absorption capacity under a load tend to oppose each other. Generally, in order to obtain a high water-retention capacity, the crosslinking density of the water-absorbent resin must be lowered. However, a reduction in crosslinking density lowers the gel strength, resulting in a reduction in the water-absorption capacity under a load. Further, a reduction in the crosslinking density of a water-absorbent resin increases non-crosslinked components. Therefore, when the resin is brought into contact with a fluid, the water soluble component is likely to be dissolved. As a result, when the resin is used in a hygienic material, etc., a rash may be caused due to the water soluble component.

As a technique for improving the properties of water-absorbent resin, a method for performing reversed-phase suspension polymerization using a specific amount of a specific surfactant (see Patent Literature 1); a method for performing reversed-phase suspension polymerization in two or more steps (see Patent Literature 2); a method for performing reversed-phase suspension polymerization using a specific amount of a persulfate as a polymerization initiator (see Patent Literature 3); and a method for using a water-soluble azo initiator for radical polymerization in the presence of a specific internal-crosslinking agent (see Patent Literature 4), and the like, are proposed.

However, the water-absorbent resins produced by the methods disclosed in Patent Literature 1 to 3 cannot sufficiently satisfy all of the properties, i.e., a high water-retention capacity, a high water-absorption capacity under a load, and a small amount of water soluble component. Further, in the reversed-phase suspension polymerization disclosed in the Examples of Patent Literature 4, a water-soluble azo initiator for radical polymerization is used in a large amount, which causes heat generation or a rapid reaction, resulting in the organic solvent being released to the outside of the reaction system; thus, the environmental impact is not considered therein.

CITATION LIST

Patent Literature

PTL 1: Japanese Unexamined Patent Publication No. H6-345819
PTL 2: Japanese Unexamined Patent Publication No. H3-227301
PTL 3: Japanese Unexamined Patent Publication No. H6-287233
PTL 4: Japanese Unexamined Patent Publication No. 2006-176570

SUMMARY OF INVENTION

Technical Problem

The present invention has been made in view of the current state of the aforementioned prior art. A principal object of the present invention is to provide a novel method for producing a water-absorbent resin using reversed-phase suspension polymerization, by which the environmental impact can be lessened by reducing the amount of petroleum hydrocarbon dispersion medium released to the outside of the system, and which makes it possible to obtain a water-absorbent resin having a high water-retention capacity and water-absorption capacity under a load at the same time, and also having a small amount of water soluble component, and to provide a water-absorbent resin obtained by the method.

Solution to Problem

The present inventors conducted extensive research to achieve the above object. As a result, the inventors found that by using a specific amount of a water-soluble azo initiator for radical polymerization as a polymerization initiator, and by performing reversed-phase suspension polymerization of a water-soluble ethylenic unsaturated monomer in the presence of a specific amount of a hypophosphorous compound, the amount of organic solvent released to the outside of the reaction system can be reduced, and a water-absorbent resin having at the same time a high water-retention capacity, a high water-absorption capacity under a load, and a small amount of water soluble component can be produced. Thereby, the present invention has been accomplished.

More specifically, the present invention provides a method for producing a water-absorbent resin, and a water-absorbent resin obtained by the method, as described below.

Item 1. A method for producing a water-absorbent resin comprising:

subjecting at least one water-soluble ethylenic unsaturated monomer to reversed-phase suspension polymerization in a petroleum hydrocarbon dispersion medium, the reversed-phase suspension polymerization being conducted using 0.00005 to 0.00016 mol of water-soluble azo initiator for radical polymerization per mol of the water-soluble ethylenic unsaturated monomer to be used in the presence of 0.000015 to 0.00015 mol of hypophosphorous compound per mol of the water-soluble ethylenic unsaturated monomer to be used.

Item 2. The method for producing a water-absorbent resin according to Item 1, wherein the water-soluble azo initiator for radical polymerization is at least one member selected from the group consisting of 2,2'-azobis(2-amidinopropane) dihydrochloride, 2,2'-azobis{2-[1-(2-hydroxyethyl)-2-imidazolin-2-yl]propane}dihydrochloride, and 2,2'-azobis[N-(2-carboxyethyl)-2-methylpropioneamidine]tetrahydrate.

Item 3. The method for producing a water-absorbent resin according to Item 1 or 2, wherein the hypophosphorous compound is at least one member selected from the group consisting of hypophosphorous acid and sodium hypophosphite.

Item 4. The method for producing a water-absorbent resin according to any one of Items 1 to 3, wherein the water-soluble ethylenic unsaturated monomer is at least one member selected from the group consisting of (meth)acrylic acid and salts thereof.

Item. 5 The method for producing a water-absorbent resin according to any one of Items 1 to 4, wherein the reversed-phase suspension polymerization is conducted in two or more steps.

Item. 6 The method for producing a water-absorbent resin according to any one of Items 1 to 5, wherein post-crosslinking is conducted by adding a cross-linking agent after the completion of the reversed-phase suspension polymerization of the water-soluble ethylenic unsaturated monomer.

Item 7. A water-absorbent resin produced by any one of the methods of Items 1 to 6.

The method for producing a water-absorbent resin of the present invention is described in detail below.

Method for Producing Water-Absorbent Resin

The method for producing a water-absorbent resin of the present invention comprises subjecting a water-soluble ethylenic unsaturated monomer to reversed-phase suspension polymerization in a petroleum hydrocarbon dispersion medium, the reversed-phase suspension polymerization being conducted using a specific amount of a water-soluble azo initiator for radical polymerization as a polymerization initiator in the presence of a specific amount of a hypophosphorous compound.

According to this method, by using a specific amount of a water-soluble azo initiator for radical polymerization as a polymerization initiator, the amount of the petroleum hydrocarbon dispersion medium released to the outside of the reaction system can be reduced, and a reversed-phase suspension polymerization reaction can be stably performed. By further using a specific amount of a hypophosphorous compound, together with the aforementioned water-soluble azo initiator for radical polymerization, a water-absorbent resin achieving excellent properties simultaneously, i.e., a high water-retention capacity and water-absorption capacity under a load, and a small amount of water soluble component, can be obtained.

The method for producing a water-absorbent resin of the present invention is described in detail below.

(1) Starting Compound (i) Water-Soluble Ethylenic Unsaturated Monomer

The production method of the present invention uses a water-soluble ethylenic unsaturated monomer as a starting material. Examples of the water-soluble ethylenic unsaturated monomer include (meth)acrylic acid (as used herein, "acryl" and "methacryl" collectively refer to "(meth)acryl;" the same applies hereinafter) and salts thereof; 2-(meth)acrylamide-2-methylpropanesulfonic acid and salts thereof; (meth)acrylamide, N,N-dimethyl(meth)acrylamide, 2-hydroxyethyl(meth)acrylate, N-methylol(meth)acrylamide, polyethylene glycol mono(meth)acrylate, and like nonionic monomers; N,N-diethylaminoethyl(meth)acrylate, N,N-diethylaminopropyl(meth)acrylate, diethylaminopropyl(meth)acrylamide, and like amino group-containing unsaturated monomers, and quaternary compounds thereof. These water-soluble ethylenic unsaturated monomers may be used singly, or in a combination of two or more thereof.

Of these, (meth)acrylic acid, salts thereof, (meth)acrylamide, N,N-dimethylacrylamide, and the like, are preferable, and (meth)acrylic acid, salts thereof, and the like, are more preferable, because they are easily available industrially.

The aforementioned water-soluble ethylenic unsaturated monomer can be used in an aqueous solution to increase the dispersion efficiency in a petroleum hydrocarbon dispersion medium when reversed-phase suspension polymerization is conducted. The concentration of the monomer in such an aqueous solution is not particularly limited, and is usually 20% by mass or more to a saturated concentration or less, preferably 25 to 70% by mass, and more preferably 30 to 55% by mass.

When the water-soluble ethylenic unsaturated monomer contains an acid group as in (meth)acrylic acid, 2-(meth)acrylamide-2-methylpropanesulfonic acid, or the like, those in which the acid group has been neutralized in advance with an alkaline neutralizing agent may be used, if necessary. Examples of such alkaline neutralizing agents include, but are not particularly limited to, sodium hydroxide, potassium hydroxide, and like alkali metal compounds; ammonia and the like. In particular, these alkaline neutralizing agents can be used in the form of an aqueous solution to simplify the neutralization. The aforementioned alkaline neutralizing agents may be used singly, or in a combination of two or more thereof.

The degree of neutralization of the water-soluble ethylenic unsaturated monomer with an alkaline neutralizing agent is not particularly limited. The degree is considered as the degree of neutralization of all the acid groups of the water-soluble ethylenic unsaturated monomer, and is usually 10 to 100% by mol, and more preferably 30 to 80% by mol, in order to increase the osmotic pressure of the resulting water-absorbent resin and to thereby improve the absorption property thereof, and also in order not to cause any disadvantages in safety or the like due to the presence of an excess alkaline neutralizing agent.

(ii) Petroleum Hydrocarbon Dispersion Medium

Examples of usable petroleum hydrocarbon dispersion media include n-hexane, n-heptane, 2-methylhexane, 3-methylhexane, 2,3-dimethylpentane, 3-ethylpentane, n-octane, and like aliphatic hydrocarbons; cyclohexane, methylcyclohexane, cyclopentane, methylcyclopentane, trans-1,2-dimethylcyclopentane, cis-1,3-dimethylcyclopentane, trans-1,3-dimethylcyclopentane, and like alicyclic hydrocarbons; and benzene, toluene, xylene, and like aromatic hydrocarbons. These petroleum hydrocarbon dispersion media may be used singly, or in a combination of two or more thereof. Examples of a mixed hydrocarbon dispersion medium comprising a mixture of two or more petroleum hydrocarbon dispersion media include Exxsol Heptane (produced by Exxon Mobil Corporation, a mixed hydrocarbon dispersion medium containing, as main components, n-heptane, 2-methylhexane, 3-methylhexane, and methylcyclohexane). Of these petroleum hydrocarbon dispersion media, n-hexane, n-heptane, cyclohexane, Exxsol Heptane, and the like, are preferable because they are easily available industrially, stable in quality, and inexpensive.

The amount of the petroleum hydrocarbon dispersion medium is not particularly limited. In order to easily remove the heat of polymerization and to control the reaction temperature in the reversed-phase suspension polymerization, the petroleum hydrocarbon dispersion medium is used in an amount of preferably 50 to 600 parts by mass, and more preferably 100 to 550 parts by mass, relative to 100 parts by mass of the water-soluble ethylenic unsaturated monomer.

(iii) Dispersion Stabilizer

As a dispersion stabilizer used in the reversed-phase suspension polymerization, a surfactant may be used. Examples of usable surfactants include sucrose fatty acid esters, polyglyceryl fatty acid esters, sorbitan fatty acid esters, polyoxyethylene sorbitan fatty acid esters, polyoxyethylene glycerine fatty acid esters, sorbitol fatty acid esters, polyoxyethylene sorbitol fatty acid esters, polyoxyethylene alkyl ethers, polyoxyethylene alkyl phenyl ethers, polyoxyethylene castor oil, polyoxyethylene hydrogenated castor oil, alkyl allyl formaldehyde-condensed polyoxyethylene ethers, polyoxyethylene polyoxypropylene block copolymers, polyoxyethylene polyoxypropyl alkyl ethers, polyethylene glycol fatty acid esters, alkyl glucosides, N-alkyl gluconamides, polyoxyethylene fatty acid amides, polyoxyethylene alkylamines, phosphates of polyoxyethylene alkyl ethers, phosphates of polyoxyethylene alkyl allyl ethers, and the like. Of these, sorbitan fatty acid esters, polyglyceryl fatty acid esters, sucrose fatty acid esters, and the like, are preferable, in terms of the dispersion stability of an aqueous monomer solution. These surfactants may be used singly, or in a combination of two or more thereof.

The surfactant is used in an amount of 0.1 to 5 parts by mass, preferably 0.2 to 3 parts by mass, relative to 100 parts by mass of the water-soluble ethylenic unsaturated monomer, so that in the petroleum hydrocarbon dispersion medium, an excellent dispersion state of the water-soluble ethylenic unsaturated monomer is maintained, and a dispersion effect that corresponds to the amount used is obtained.

Together with a surfactant, a polymeric dispersion agent can be used as a dispersion stabilizer. Examples of usable polymeric dispersion agents include maleic anhydride-modified polyethylene, maleic anhydride-modified polypropylene, maleic anhydride-modified ethylene-propylene copolymer, maleic anhydride-modified EPDM (ethylene-propylene-diene-terpolymer), maleic anhydride-modified polybutadiene, maleic anhydride-ethylene copolymer, maleic anhydride-propylene copolymer, maleic anhydride-ethylene-propylene copolymer, maleic anhydride-butadiene copolymer, polyethylene, polypropylene, ethylene-propylene copolymer, oxidized polyethylene, oxidized polypropylene, oxidized ethylene-propylene copolymer, ethylene-acrylic acid copolymer, ethyl cellulose, ethyl hydroxyethyl cellulose, and the like. Of these, maleic anhydride-modified polyethylene, maleic anhydride-modified polypropylene, maleic anhydride-modified ethylene-propylene copolymer, maleic anhydride-ethylene copolymer, maleic anhydride-propylene copolymer, maleic anhydride-ethylene-propylene copolymer, polyethylene, polypropylene, ethylene-propylene copolymer, oxidized polyethylene, oxidized polypropylene, oxidized ethylene-propylene copolymer, and the like, are preferable, in terms of the dispersion stability of the aqueous monomer solution. These polymeric dispersion agents may be used singly, or in a combination of two or more thereof.

The polymeric dispersion agent is used in an amount of preferably 0.1 to 5 parts by mass, more preferably 0.2 to 3 parts by mass, relative to 100 parts by mass of the water-soluble ethylenic unsaturated monomer, so that in the petroleum hydrocarbon dispersion medium, an excellent dispersion state of the water-soluble ethylenic unsaturated monomer is maintained, and a dispersion effect that corresponds to the amount used is obtained.

(iv) Water-Soluble Azo Initiator for Radical Polymerization

The present invention requires the use of a water-soluble azo initiator for radical polymerization as a polymerization initiator. As the water-soluble azo initiator for radical polymerization, either an azo compound that exhibits water solubility as is or an azo compound that exhibits water solubility when neutralized to salt may be used.

By using such a water-soluble azo initiator for radical polymerization in an amount within the specific range mentioned below, the polymerization reaction can stably proceed, and a water-absorbent resin having excellent properties can thereby be obtained. In addition, a rapid polymerization reaction can be prevented, thereby reducing the amount of petroleum hydrocarbon dispersion medium released to the outside of the reaction system.

Specific examples of the water-soluble azo initiator for radical polymerization usable in the present invention include azo compounds, such as 1-{(1-cyano-1-methylethyl)azo}formamide, 2,2'-azobis[2-(N-phenylamidino) propane] dihydrochloride, 2,2'-azobis{2-[N-(4-chlorophenyl) amidino]propane}dihydrochloride, 2,2'-azobis{2-[N-(4-hydroxyphenyl)amidino]propane}dihydrochloride, 2,2'-azobis[2-(N-benzylamidino)propane]dihydrochloride, 2,2'-azobis[2-(N-allylamidino)propane]dihydrochloride, 2,2'-azobis(2-amidinopropane)dihydrochloride, 2,2'-azobis{2-[N-(2-hydroxyethyl)amidino]propane}dihydrochloride, 2,2'-azobis[2-(5-methyl-2-imidazolin-2-yl)propane]dihydrochloride, 2,2'-azobis[2-(2-imidazolin-2-yl)propane]dihydrochloride, 2,2'-azobis[2-(4,5,6,7-tetrahydro-1H-1,3-diazepin-2-yl)propane]dihydrochloride, 2,2'-azobis[2-(5-hydroxy-3,4,5,6-tetrahydropyrimidin-2-yl)propane] dihydrochloride, 2,2'-azobis{2-[1-(2-hydroxyethyl)-2-imidazolin-2-yl]propane}dihydrochloride, 2,2'-azobis[2-(2-imidazolin-2-yl)propane], 2,2'-azobis{2-methyl-N-[1,1-bis (hydroxymethyl)-2-hydroxyethyl]propionamide}, 2,2'-azobis{2-methyl-N-[1,1-bis(hydroxymethyl)ethyl] propionamide}, 2,2'-azobis[2-methyl-N-(2-hydroxyethyl) propionamide], 2,2'-azobis(2-methylpropionamide) dihydrochloride, 4,4'-azobis-4-cyanovaleric acid, 2,2'-azobis [2-(hydroxymethyl)propionitrile], 2,2'-azobis[2-(2-imidazolin-2-yl)propane]disulfate dihydrate, 2,2'-azobis[N-(2-carboxyethyl)-2-methylpropioneamidine]tetrahydrate, and 2,2'-azobis[2-methyl-N-(2-hydroxyethyl)propionamide]. Of these, 2,2'-azobis(2-amidinopropane)dihydrochloride, 2,2'-azobis{2-[1-(2-hydroxyethyl)-2-imidazolin-2-yl]propane}dihydrochloride, 2,2'-azobis[N-(2-carboxyethyl)-2-methylpropioneamidine]tetrahydrate, and the like, are preferable, considering that they allow the polymerization temperature, etc., in the polymerization reaction to be easily adjusted, and that they enable a water-absorbent resin having a high water-retention capacity and water-absorption capacity under a load, and a small amount of water soluble component, to be obtained. These water-soluble azo initiators for radical polymerization may be used singly, or in a combination of two or more thereof.

The water-soluble azo initiator for radical polymerization is used in an amount of 0.00005 to 0.00016 mol, preferably 0.00007 to 0.00013 mol, per mol of the water-soluble ethylenic unsaturated monomer. An amount of initiator exceeding the aforementioned range is not preferable because such an amount of initiator causes a rapid polymerization reaction, allowing the petroleum hydrocarbon dispersion medium to be easily released to the outside of the reaction system. In contrast, the use of a too small amount of the initiator is not preferable because such an amount of initiator requires a considerably long time for the polymerization reaction, and also makes the polymerization reaction unstable, allowing the polymer of the water-soluble ethylenic unsaturated monomer to easily aggregate.

(v) Hypophosphorous Compound

The present invention provides a water-absorbent resin having a high water-retention capacity, a high water-absorption capacity under a load, and a low content of water soluble component, by subjecting a water-soluble ethylenic unsaturated monomer to reversed-phase suspension polymerization in the presence of a hypophosphorous compound in a specific amount of monomer described below.

Examples of usable hypophosphorous compounds include hypophosphorous acid, sodium hypophosphite, potassium hypophosphite, calcium hypophosphite, barium hypophosphite, ammonium hypophosphite, and the like. Of these, hypophosphorous acid and sodium hypophosphite are preferable from the viewpoint that these compounds are industrially easily available and can produce a water-absorbent resin having a high water-retention capacity, a high water-absorption capacity under a load, and a low content of water soluble component. These hypophosphorous compounds may be used singly, or in a combination of two or more thereof.

The amount of hypophosphorous compound used must be 0.000015 to 0.00015 mol per mole of water-soluble ethylenic unsaturated monomer, with 0.000025 to 0.00012 mol being preferable. When the amount of the hypophosphorous compound used is too small, the resulting water-absorbent resin is likely to have poor water-retention capacity and water-absorption capacity under a load. When the amount used is too large, it increases the content of water soluble component.

(vi) Internal-Crosslinking Agent

In the present invention, a crosslinking agent may be used if necessary when a water-soluble ethylenic unsaturated monomer is subjected to reversed-phase suspension polymerization. The type of such crosslinking agent (hereinafter referred to as an "internal-crosslinking agent") is not particularly limited. For example, a compound having two or more polymerizable unsaturated groups may be used. Specific examples of such compounds include di- or tri(meth)acrylic esters of polyols, such as (poly)ethylene glycol (herein, for example, "polyethylene glycol" and "ethylene glycol" are collectively referred to as "(poly)ethylene glycol"; the same applies hereinafter), (poly) propylene glycol, trimethylolpropane, glycerol polyoxyethylene glycol, polyoxypropylene glycol, and (poly)glycerol; unsaturated polyesters obtained by reacting the above-mentioned polyol with an unsaturated acid, such as maleic acid or fumaric acid; bisacrylamides, such as N,N'-methylenebis(meth)acrylamide; di- or tri(meth)acrylic esters obtained by reacting a polyepoxide with a (meth)acrylic acid; carbamyl esters of di(meth)acrylic acid obtained by reacting a polyisocyanate, such as tolylenediisocyanate or hexamethylenediisocyanate with hydroxyethyl (meth)acrylate; allylated starch; allylated cellulose; diallyl phthalate; N,N',N''-triallyl isocyanurate; and divinylbenzene.

In addition to the above-described compounds having two or more polymerizable unsaturated groups, compounds having two or more other reactive functional groups may also be used as the internal-crosslinking agent. Examples of such internal-crosslinking agents include glycidyl-group-containing compounds, such as (poly)ethylene glycol diglycidyl ethers, (poly)propylene glycol diglycidyl ethers, and (poly)glycerol diglycidyl ethers; (poly)ethylene glycol; (poly)propylene glycol; (poly)glycerol; pentaerythritol; ethylenediamine; polyethyleneimine; glycidyl(meth)acrylate; and the like. These internal-crosslinking agents may be used singly, or in a combination of two or more thereof.

In particular, (poly)ethylene glycol diglycidyl ethers, (poly)propylene glycol diglycidyl ethers, (poly)glycerol diglycidyl ethers, N,N'-methylenebisacrylamide, and the like are preferable in terms of high reactivity at low temperatures.

Although the internal-crosslinking agent may be added to a dispersion medium, the internal-crosslinking agent is preferably added to the above-described monomer in order to efficiently demonstrate the effect produced by the internal-crosslinking agent.

When the internal-crosslinking agent is used, the amount used is preferably 0.0000001 to 0.01 mol and more preferably 0.000001 to 0.005 mol per mole of water-soluble ethylenic unsaturated monomer, in order to improve the water-absorption properties of the resulting water-absorbent resin.

(2) Reversed-Phase Suspension Polymerization Method

In the present invention, a water-soluble ethylenic unsaturated monomer may be polymerized by the reversed-phase suspension polymerization method using a specific amount of a water-soluble azo initiator for radical polymerization in a petroleum hydrocarbon dispersion medium containing the above-described dispersion stabilizer in the presence of a specific amount of the above-described hypophosphorous compound. At this time, the above-described internal-crosslinking agent may be used, if necessary.

In the method of the present invention for producing a water-absorbent resin, water in an amount of 10 to 200 parts by mass may be used relative to 100 parts by mass of the above-described petroleum hydrocarbon dispersion medium. The amount of water used is preferably 10 parts by mass or more from the viewpoint of improving the dispersion state of the water-soluble ethylenic unsaturated monomer. Also, the amount of water used is preferably 200 parts by mass or less from the viewpoint of improving industrial production, which is economically desirable.

Although the reaction temperature of the polymerization reaction varies depending on the water-soluble azo initiator for radical polymerization used, it is not preferable when the reaction temperature is too low (below 20° C.), because the polymerization time will be long. The upper limit of the reaction temperature is preferably 110° C. in order to remove the heat of polymerization and perform a smooth polymerization reaction. From these viewpoints, the reaction temperature is usually 20 to 110° C., and preferably 40 to 90° C. Usually, the reaction time is preferably 0.1 to 4 hours.

In the present invention, the reversed-phase suspension polymerization may be performed in one step or in multiple steps of two or more. The number of steps is preferably 2 or 3 from the viewpoint of improving productivity.

Reversed-phase suspension polymerization in each of the second and subsequent steps may be performed by the same method as in the first step by mixing a water-soluble ethylenic unsaturated monomer with the reaction mixture obtained by the polymerization reaction in the first step after reversed-phase suspension polymerization in the first step is performed by the above-described method. The reversed-phase suspension polymerization in each of the second and subsequent steps may be performed under the same conditions as described in the above method by adding a water-soluble azo initiator for radical polymerization, a hypophosphorous compound, and an internal-crosslinking agent (which is added if necessary), in addition to the water-soluble ethylenic unsaturated monomer, in the above-mentioned range of molar ratio of each component relative to the water-soluble ethylenic unsaturated monomer, based on the amount of the water-soluble ethylenic unsaturated monomer added during reversed-phase suspension polymerization in each of the second and subsequent steps.

(3) Post-Crosslinking

In the present invention, post-crosslinking treatment is carried out by adding a post-crosslinking agent in the process after the completion of polymerization of the water-soluble ethylenic unsaturated monomer and before drying of the resulting resin, thereby increasing the crosslinking density of the surface portion and making it possible to obtain a water-absorbent resin having improved water-absorption properties, such as the water-absorption capacity under a load and the gel strength, and being suitable for hygienic materials. Compounds having two or more reactive functional groups can be used as such post-crosslinking agents. Examples thereof include polyols, such as ethylene glycol, propylene glycol, 1,4-butanediol, trimethylolpropane, glycerol, polyoxyethylene glycol, polyoxypropylene glycol, and polyglycerol; polyglycidyl compounds, such as (poly)ethylene glycol diglycidyl ethers, (poly)ethylene glycol triglycidyl ether, (poly)glycerol diglycidyl ether, (poly)glycerol triglycidyl ether, (poly)propylene glycol polyglycidyl ether, and (poly)glycerol polyglycidyl ether; haloepoxy compounds, such as epichlorohydrin, epibromohydrin, and α-methylepichlorohydrin; compounds having two or more reactive functional groups, for example, isocyanate compounds, such as 2,4-tolylenediisocyanate and hexamethylenediisocyanate; oxetane compounds, such as 3-methyl-3-oxetane methanol, 3-ethyl-3-oxetane methanol, 3-butyl-3-oxetane methanol, 3-methyl-3-oxetane ethanol, 3-ethyl-3-oxetane ethanol, and 3-butyl-3-oxetane ethanol; oxazoline compounds, such as 1,2-ethylene bisoxazoline; and carbonate compounds, such as ethylene carbonate. Of these, polyglycidyl compounds, such as (poly)ethylene glycol diglycidyl ethers, (poly)ethylene glycol triglycidyl ether, (poly)glycerol diglycidyl ethers, (poly)glycerol triglycidyl ether, (poly)propylene glycol polyglycidyl ether, and (poly)glycerol polyglycidyl ether are particularly preferable. These post-crosslinking agents may be used singly, or in a combination of two or more thereof.

The post-crosslinking agent is added in an amount preferably in the range of 0.00005 to 0.01 mol and more preferably 0.0001 to 0.005 mol per mole of the total amount of water-soluble ethylenic unsaturated monomer used in reversed-phase suspension polymerization reaction, in order to prevent a reduction in the water-absorption capacity of the resulting water-absorbent resin and to increase the crosslinking density on or near the surface to improve the various properties.

The timing for adding the post-crosslinking agent is not particularly limited as long as it is added after polymerization is completed. The post-crosslinking agent is preferably added in the presence of 1 to 400 parts by mass of water, more preferably 5 to 200 parts by mass of water, and most preferably 10 to 100 parts by mass of water relative to 100 parts by mass of solids of the water-absorbent resin.

When the post-crosslinking agent is used, water or a hydrophilic organic solvent may be used as a solvent, if necessary. Examples of hydrophilic organic solvents include lower alcohols, such as methyl alcohol, ethyl alcohol, n-propyl alcohol, and isopropyl alcohol; ketones, such as acetone and methyl ethyl ketone; ethers, such as diethyl ether, dioxane, and tetrahydrofuran; amides, such as N,N-dimethylformamide; sulfoxides, such as dimethyl sulfoxide; and the like. These hydrophilic organic solvents may be used singly, or in a combination of two or more thereof. The hydrophilic organic solvent may also be used as a mixed solvent with water.

The reaction temperature in the post-crosslinking reaction is preferably 50 to 250° C., more preferably 60 to 180° C., yet more preferably 60 to 140° C., and still more preferably 70 to 120° C. Further, although the post-crosslinking reaction time cannot be generally specified because it varies depending on the reaction temperature, type and amount of the crosslinking agent, etc., the post-crosslinking reaction time is typically 1 to 300 minutes and preferably 5 to 200 minutes.

(4) Drying

In the present invention, the drying may be carried out under normal pressure or reduced pressure, and may also be carried out under a nitrogen stream or the like in order to increase the drying efficiency. When the drying is carried out under normal pressure, the drying temperature is preferably 70 to 250° C., more preferably 80 to 180° C., yet more preferably 80 to 140° C., and still more preferably 90 to 130° C. When the drying is carried out under reduced pressure, the drying temperature is preferably 60 to 100° C., more preferably 70 to 90° C.

Water-Absorbent Resin

In regard to the water-absorbent resin obtained by the above-described method, the water-absorbent resin after drying preferably has a water content of 20% or less, more preferably 1 to 15%, and still more preferably 3 to 10%, in order to provide flowability. Further, amorphous silica powder may be added in order to improve the flowability.

The water-retention capacity of saline solution of the water-absorbent resin of the present invention is preferably 40 to 60 g/g and more preferably 40 to 50 g/g, in order to increase the absorption capacity and to decrease the amount of re-wetting of fluid when the water-absorbent resin is used in hygienic materials.

Further, the water-absorption capacity of saline solution under a load of 4.14 kPa of the water-absorbent resin of the present invention is preferably 15 mL/g or more and more preferably 20 mL/g or more, in order to decrease the amount of re-wetting when the water-absorbent resin is used in hygienic materials and pressure is applied to the hygienic materials after the absorption of fluid.

The content of water soluble component in the water-absorbent resin of the present invention is preferably 20% by mass or less and more preferably 18% by mass or less, in order to prevent a slimy, viscous fluid from sticking to the skin when the water-absorbent resin is used in hygienic materials.

The median particle size of the water-absorbent resin suitable for absorbent materials and absorbent articles that use the same is preferably 200 to 600 μm, more preferably 250 to 550 μm, and still more preferably 300 to 500 μm.

The above-described water content, water-retention capacity of saline solution, water-absorption capacity of saline solution under a load of 4.14 kPa, content of water soluble component and median particle size of the water-absorbent resin are values determined by the measurement methods described in the examples (described below).

Advantageous Effect of the Invention

According to the method of the present invention for producing a water-absorbent resin, environmental impact can be lessened by reducing the amount of petroleum hydrocarbon dispersion medium released to the outside of the system, and the water-absorbent resin formed by the method has excellent properties, such as a high water-retention capacity, a high water-absorption capacity under a load, and a low content of water soluble component. Therefore, the water-absorbent resin obtained by the method of the present invention can be suitably used in hygienic materials, such as disposable diapers.

DESCRIPTION OF EMBODIMENTS

The present invention is explained in detail below with reference to Examples and Comparative Examples; however, the present invention is not limited to the Examples below.

The water-absorbent resin obtained in each Example and Comparative Example was evaluated in terms of the water content, water-retention capacity of saline solution, water-absorption capacity of saline solution under load of 4.14 kPa, content of water soluble component, and median particle size by the following methods.

<Water Content>

About 2 g of the water-absorbent resin was precisely weighed out (Wa (g)) in a previously weighed aluminum foil case (No. 8). The above sample was dried for 2 hours in a hot air oven (produced by ADVANTEC) set at an internal temperature of 105° C. Thereafter, the dried sample was allowed to cool in a desiccator, and the mass Wb (g) of the dried water-absorbent resin was determined. The water content of the water-absorbent resin was calculated by the following equation:

Water content(%)=$[Wa-Wb]/Wa \times 100$

<Water-Retention Capacity of Saline Solution>

500 g of a 0.9% by mass aqueous solution of sodium chloride (saline solution) was weighed out in a 500-mL beaker. 2.0 g of water-absorbent resin was dispersed therein so as not to form lumps while stirring the solution at 600 rpm. The solution was left to stand for 30 minutes in a stirred state to sufficiently swell the water-absorbent resin. Subsequently, the solution was poured into a cotton bag (Cottonbroad No. 60, 100 mm (W)×200 mm (H)), and the upper part of the cotton bag was closed with a rubber band. The cotton bag was dehydrated for 1 minute using a dehydrator (produced by Kokusan Co., Ltd., product number: H-122) that was set at a centrifugal force of 167 G, and the mass We (g) of the dehydrated cotton bag containing swollen gel was measured. The same procedure was repeated without adding the water-absorbent resin, and the mass Wd (g) of the dehydrated empty cotton bag was measured. The water-retention capacity was calculated by the following equation:

Water-retention capacity of saline solution (g/g)= $[Wc-Wd]$(g)/mass of the water-absorbent resin(g)

<Water-Absorption Capacity of Saline Solution Under Load of 4.14 kPa>

Figure 1:
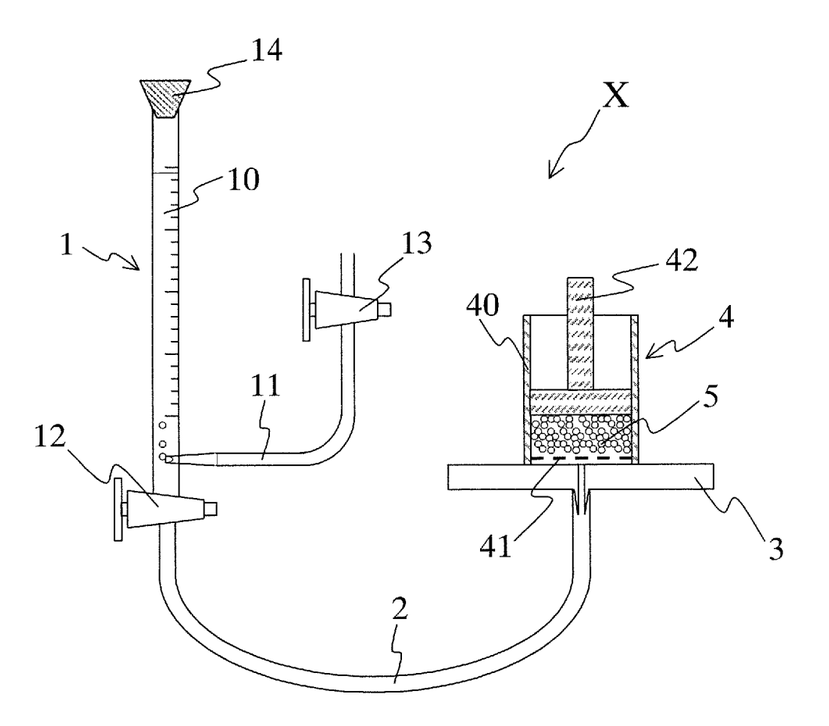
FIG. 1 A schematic view showing a general structure of a device for measuring the water-absorption capacity under a load.

The water-absorption capacity of saline solution under a load of 4.14 kPa of water-absorbent resin was measured using a measuring device X schematically shown in FIG. 1.

The measuring device X shown in FIG. 1 comprises a burette section 1, a tube 2, a measuring board 3, and a measuring section 4 placed on the measuring board 3. The burette section 1 includes a rubber plug 14 connected to the top of a burette 10, and an air introduction tube 11 and a cock 12, which are connected to the lower portion of the burette 10. Further, the air introduction tube 11 has a cock 13 at the upper portion thereof. The tube 2 is provided between the burette section 1 and the measuring board 3. The tube 2 has a diameter of 6 mm. A 2-mm-diameter hole is formed in the center of the measuring board 3, and the tube 2 is connected to the hole. The measuring section 4 has a cylinder 40, a nylon mesh 41 adhered to the bottom of the cylinder, and a weight 42. The cylinder 40 has an inner diameter of 2.0 cm. The nylon mesh 41 has openings of 75 μm (200 mesh). Water-absorbent resin 5 is evenly spread over the nylon mesh 41 at the time of measurement. The weight 42 has a diameter of 1.9 cm and a mass of 119.6 g. The weight 42 is placed on the water-absorbent resin 5 so that a load of 4.14 kPa can be uniformly applied to the water-absorbent resin 5.

The measurement using device X having such a structure was performed as described below. First, the cock 12 and the cock 13 at the burette section 1 were closed, saline solution adjusted to 25° C. was poured from the top of the burette 10, and the top of the burette was plugged with the rubber plug 14. Thereafter, the cock 12 and the cock 13 at the burette section 1 were opened. Next, the height of the measuring board 3 was adjusted so that the level of the end of the tube 2 at the central portion of the measuring board 3 became the same as that of the air inlet of the air introduction tube 11.

Separately, 0.10 g of the water-absorbent resin 5 was evenly dispersed over the nylon mesh 41 in the cylinder 40, and the weight 42 was placed on the water-absorbent resin 5. Subsequently, the measuring section 4 was placed so that its center was aligned with the tube opening in the center of the measuring board 3.

When the water-absorbent resin 5 started absorbing water, the amount of reduction in saline solution in the burette 10 (i.e., the volume of saline solution absorbed by the water-absorbent resin 5: We (mL)) was continuously read off. The water-absorption capacity of saline solution under the load of the water-absorbent resin 5 at 60 minutes after the start of water absorption was determined by the following equation:

Water-absorption capacity of saline solution under a load of 4.14 kPa(ml/g)=$We$ (mL)/0.10 (g)

<Content of Water Soluble Component>

To a 500-mL beaker, 500±0.1 g of saline solution was weighed, a magnetic stirrer bar (8 mm (diameter)×30 mm, without ring) was placed therein, and the beaker was placed on a magnetic stirrer (produced by Iuchi, model number: HS-30D). Subsequently, the rotation of the magnetic stirrer bar was adjusted to 600 rpm, and the bottom of the vortex generated by the rotation of the magnetic stirrer bar was adjusted so that it was located right above the magnetic stirrer bar.

Subsequently, 2.0±0.002 g of water-absorbent resin was dispersed by being quickly added between the center portion of the vortex in the beaker and the sidewall of the beaker, followed by stirring for 3 hours. The water-absorbent resin dispersion after stirring for 3 hours was filtered through a standard sieve (openings of 75 µm) and the resulting filtrate was further subjected to filtration under reduced pressure using Kiriyama-rohto (filter paper; produced by ADVANTEC, model number: No. 6).

80±0.0005 g of the resulting filtrate was weighed in a 100-mL beaker having a constant weight and dried in a hot air oven (produced by ADVANTEC, model number: FV-320) set at an internal temperature of 140° C. until it reached a constant weight. Thereafter, the mass Wf (g) of the solids content of the filtrate was measured.

The procedure described above was performed without using the water-absorbent resin to measure the mass Wg (g) of the solids content of the filtrate, and the content of water soluble component was calculated by the following equation:

Content of water soluble component(% by mass)= [[(Wf−Wg)×(500/80)]/2]×100

<Median Particle Size>

0.25 g of amorphous silica (Degussa Japan, Sipernat 200) was mixed as a lubricant with 50 g of a water-absorbent resin.

JIS standard sieves having openings of 850 µm, 600 µm, 500 µm, 425 µm, 300 µm, 250 µm, and 150 µm, and a receiving tray were combined in that order from the top. Water-absorbent resin were placed on the top sieve of the combined sieves, and shaken for 20 minutes using a Ro-Tap Sieve Shaker to conduct classification.

After classification, the mass of the water-absorbent resin remaining on each sieve was calculated as the mass percentage relative to the total mass, and the mass percentage was integrated in descending order of particle size. Thereby, the relationship between the sieve opening and the integrated value of the mass percentage of the water-absorbent resin remaining on the sieve was plotted on a logarithmic probability paper. By connecting the plots on the probability paper with straight lines, the particle size corresponding to the 50% percentile of the integrated mass percentage was obtained as the median particle size.

Example 1

A 2-L cylindrical round-bottomed separable flask having an internal diameter of 110 mm, equipped with a stirrer, a two pitched paddle impeller, a reflux condenser (cooling part: Allihn condenser, length: 60 cm), a dropping funnel, and a nitrogen gas inlet tube was prepared in a draft chamber. In the cooling part, a coolant having a temperature of 5° C. was circulated using a cooling water circulation apparatus (produced by Tokyo Rikakikai Co., Ltd.: EYELA COOL ACE CA-1112).

290 g of n-heptane was placed into the flask, and 0.74 g of a sucrose stearate (produced by Mitsubishi-Kagaku Foods Corporation, Ryoto sugar ester S-370) and 0.74 g of a maleic anhydride-modified ethylene-propylene copolymer (produced by Mitsui Chemicals, Inc., Hi-wax 1105A) were added thereto. The temperature was raised to 80° C. while stirring to dissolve the surfactant, and thereafter the solution was cooled to 50° C.

Separately, 92 g (1.02 mol) of an 80% by mass aqueous solution of acrylic acid was placed into another 500-mL Erlenmeyer flask, and 146.0 g of a 21% by mass aqueous solution of sodium hydroxide was added dropwise thereto under external cooling to perform 75 mol % neutralization. Thereafter, 0.028 g (0.103 mmol) of 2,2'-azobis(2-amidinopropane)dihydrochloride as a radical polymerization initiator, 0.010 g (0.0649 mmol) of N,N'-methylenebisacrylamide as an internal-crosslinking agent, and 4.6 mg (0.0434 mmol) of sodium hypophosphite monohydrate as a hypophosphorous compound were added thereto and dissolved, thereby preparing an aqueous monomer solution for the first step.

The entire amount of aqueous monomer solution for the first step was added to the separable flask, and the interior of the system was sufficiently replaced with nitrogen. Thereafter, the flask was immersed in a water bath at 70° C. to raise the temperature, and the first-step polymerization was performed for 30 minutes, thereby obtaining the reaction mixture of the first step.

Separately, 128.8 g (1.43 mol) of an 80% by mass aqueous solution of acrylic acid was placed into another 500-mL Erlenmeyer flask, and 159.0 g of a 27% by mass aqueous solution of sodium hydroxide was added dropwise thereto under external cooling to perform 75 mol % neutralization. Thereafter, 0.039 g (0.144 mmol) of 2,2'-azobis(2-amidinopropane)dihydrochloride as a radical polymerization initiator, 0.012 g (0.0778 mmol) of N,N'-methylenebisacrylamide as an internal-crosslinking agent, and 6.4 mg (0.060 mmol) of sodium hypophosphite monohydrate as a hypophosphorous compound were added thereto and dissolved, thereby preparing an aqueous monomer solution for the second step.

The reaction mixture of the first step was cooled to 28° C. The aqueous monomer solution for the second step was added thereto at the same temperature, and allowed to be absorbed for 30 minutes. At the same time, the interior of the system was sufficiently replaced with nitrogen. Thereafter, the flask was again immersed in a water bath at 70° C. to raise the temperature, and the second-step polymerization was performed for 30 minutes. The n-heptane released to the outside of the flask during the reversed-phase suspension polymerization reaction was collected by a trap in the reflux condenser, and the mass thereof was measured after completing the polymerization reaction. The amount of n-heptane released to the outside of the system was 4.52 g.

After the second-step polymerization, the reaction mixture was heated using an oil bath at 125° C., and 248 g of water was distilled off to the outside of the system while refluxing n-heptane using azeotropic distillation of water and n-heptane. Thereafter, 4.42 g (0.51 mmol) of a 2% by mass aqueous solution of ethylene glycol diglycidyl ether was added thereto, and the mixture was subjected to a post-crosslinking reaction at 80° C. for 2 hours. Subsequently, the reaction mixture was heated using an oil bath at 125° C. and dried by evaporating n-heptane, thereby obtaining 230.5 g of water-absorbent resin. The water-absorbent resin had a median particle size of 400 µm and a water content of 5.1%. Table 1 shows the measurement results of each property.

Example 2

The same procedure as in Example 1 was repeated except that the amount of 2,2'-azobis(2-amidinopropane)dihydrochloride as a radical polymerization initiator used in the first step was changed to 0.020 g (0.0737 mmol), and that used in the second step was changed to 0.028 g (0.103 mmol), and the amount of sodium hypophosphite monohydrate as a hypophosphorous compound used in the first step was changed to 2.8 mg (0.0264 mmol), and that used in the second step was changed to 3.9 mg (0.0368 mmol), thereby obtaining 230.7 g of water-absorbent resin. The amount of n-heptane released to the outside of the system measured at the time of the completion of the reversed-phase suspension polymerization was 2.91 g. The water-absorbent resin had a median particle size of 400 μm and a water content of 6.0%. Table 1 shows the measurement results of each property.

Example 3

The same procedure as in Example 1 was repeated except that the amount of 2,2'-azobis(2-amidinopropane)dihydrochloride as a radical polymerization initiator used in the first step was changed to 0.035 g (0.129 mmol), and that used in the second step was changed to 0.049 g (0.181 mmol), sodium hypophosphite monohydrate as a hypophosphorous compound used in the first step was changed to 0.012 g (0.113 mmol), and that used in the second step was changed to 0.017 g (0.160 mmol), and the amount of water distilled off to the outside of the system after the completion of the second step was changed to 241 g, thereby obtaining 231.8 g of water-absorbent resin. The amount of n-heptane released to the outside of the system measured at the time of the completion of the reversed-phase suspension polymerization was 5.78 g. The water-absorbent resin had a median particle size of 390 μm and a water content of 5.8%. Table 1 shows the measurement results of each property.

Example 4

The same procedure as in Example 1 was repeated except that 2,2'-azobis[N-(2-carboxyethyl)-2-methylpropioneamidine]tetrahydrate was used as a radical polymerization initiator and the amount thereof used in the first step was adjusted to 0.035 g (0.103 mmol), and that used in the second step was adjusted to 0.049 g (0.143 mmol), thereby obtaining 229.3 g of water-absorbent resin. The amount of n-heptane released to the outside of the system measured at the time of the completion of the reversed-phase suspension polymerization was 5.53 g. The water-absorbent resin had a median particle size of 410 μm and a water content of 4.9%. Table 1 shows the measurement results of each property.

Example 5

The same procedure as in Example 1 was repeated except that the hypophosphorous compound was changed to hypophosphorous acid, the amount used in the first step was adjusted to 3.7 mg (0.0561 mmol), and that used in the second step was adjusted to 5.2 mg (0.0788 mmol), thereby obtaining 229.8 g of water-absorbent resin. The amount of n-heptane released to the outside of the system measured at the time of the completion of the reversed-phase suspension polymerization was 4.38 g. The water-absorbent resin had a median particle size of 400 μm and a water content of 5.8%. Table 1 shows the measurement results of each property.

Comparative Example 1

The same procedure as in Example 1 was repeated except that the amount of 2,2'-azobis(2-amidinopropane)dihydrochloride as a radical polymerization initiator used in the first step was changed to 9.2 mg (0.0339 mmol), and that used in the second step was changed to 0.013 g (0.0479 mmol). As a result, the polymerization reaction in the second step became unstable and the polymer of the water-soluble ethylenic unsaturated monomer aggregated. The amount of n-heptane released to the outside of the system measured at the time of the completion of the reversed-phase suspension polymerization was 2.16 g. Due to the aggregation, the properties could not be measured.

Comparative Example 2

The same procedure as in Example 1 was repeated except that the amount of 2,2'-azobis(2-amidinopropane)dihydrochloride as a radical polymerization initiator used in the first step was changed to 0.051 g (0.188 mmol), and that used in the second step was changed to 0.071 g (0.262 mmol), thereby obtaining 231.2 g of water-absorbent resin. The amount of n-heptane released to the outside of the system measured at the time of the completion of the reversed-phase suspension polymerization was 9.59 g. The water-absorbent resin had a median particle size of 380 μm and a water content of 5.2%. Table 1 shows the measurement results of each property.

Comparative Example 3

The same procedure as in Example 1 was repeated except that the amount of sodium hypophosphite monohydrate as a hypophosphorous compound used in the first step was changed to 1.0 mg (0.00943 mmol), and that used in the second step was changed to 1.4 mg (0.0132 mmol), and the amount of water distilled off to the outside of the system after the completion of the second step was changed to 252 g, thereby obtaining 228.7 g of water-absorbent resin. The amount of n-heptane released to the outside of the system measured at the time of the completion of the reversed-phase suspension polymerization was 4.65 g. The water-absorbent resin had a median particle size of 400 μm and a water content of 4.9%. Table 1 shows the measurement results of each property.

Comparative Example 4

The same procedure as in Example 3 was repeated except that the amount of 2,2'-azobis(2-amidinopropane)dihydrochloride as a radical polymerization initiator used in the first step was changed to 0.041 g (0.151 mmol), and that used in the second step was changed to 0.058 g (0.214 mmol), sodium hypophosphite monohydrate as a hypophosphorous compound used in the first step was changed to 0.019 g (0.179 mmol), and that used in the second step was changed to 0.027 g (0.255 mmol), thereby obtaining 232.1 g of water-absorbent resin. The amount of n-heptane released to the outside of the system measured at the time of the completion of the reversed-phase suspension polymerization was 7.48 g. The water-absorbent resin had a median particle size of 420 μm and a water content of 6.8%. Table 1 shows the measurement results of each property.

Comparative Example 5

The same procedure as in Example 3 was repeated except that potassium persulfate was used as the radical polymerization initiator and the amount used thereof in the first step was adjusted to 0.028 g (0.104 mmol), and that used in the second step was adjusted to 0.039 g (0.144 mmol), thereby obtaining 230.5 g of water-absorbent resin. The amount of n-heptane released to the outside of the system measured at the time of the completion of the reversed-phase suspension polymerization was 1.73 g. The water-absorbent resin had a median particle size of 410 μm and a water content of 5.2%. Table 1 shows the measurement results of each property.

TABLE 1

| | Radical polymerization initiator | | Hypophosphorous compound | |
|---|---|---|---|---|
| | Type | amount [mol[a]] | Type | amount [mol[a]] |
| Example 1 | V-50 | 0.00010 | Sodium hypophosphite | 0.000043 |
| Example 2 | V-50 | 0.000072 | Sodium hypophosphite | 0.000026 |
| Example 3 | V-50 | 0.00013 | Sodium hypophosphite | 0.00011 |
| Example 4 | VA-057 | 0.00011 | Sodium hypophosphite | 0.000043 |
| Example 5 | V-50 | 0.00010 | Hypophosphorous acid | 0.000055 |
| Comparative Example 1 | V-50 | 0.000033 | Sodium hypophosphite | 0.000043 |
| Comparative Example 2 | V-50 | 0.00018 | Sodium hypophosphite | 0.000043 |
| Comparative Example 3 | V-50 | 0.00010 | Sodium hypophosphite | 0.0000092 |
| Comparative Example 4 | V-50 | 0.00015 | Sodium hypophosphite | 0.00018 |
| Comparative Example 5 | PPS | 0.00010 | Sodium hypophosphite | 0.00011 |

| | The amount of the petroleum hydrocarbon dispersion medium released to the outside of the system [mass % [b]] | Water-absorbent resin performance | | |
|---|---|---|---|---|
| | | Water-retention capacity of saline solution [g/g] | Water-absorption capacity of saline solution under a load of 4.14 kPa [mL/g] | Water soluble component [mass %] |
| Example 1 | 1.6 | 46 | 24 | 13 |
| Example 2 | 1.0 | 48 | 20 | 12 |
| Example 3 | 2.0 | 46 | 26 | 18 |
| Example 4 | 1.9 | 48 | 21 | 17 |
| Example 5 | 1.5 | 47 | 22 | 15 |
| Comparative Example 1 | 0.7 | Immeasurable[c] | | |
| Comparative Example 2 | 3.2 | 45 | 23 | 14 |
| Comparative Example 3 | 1.6 | 46 | 11 | 12 |
| Comparative Example 4 | 2.8 | 46 | 23 | 45 |
| Comparative Example 5 | 0.6 | 48 | 13 | 24 |

[a] per mol of water-soluble ethylenic unsaturated monomer used
[b] relative to the petroleum hydrocarbon dispersion medium used in reversed-phase suspension polymerization
[c] due to aggregation of polymer <Abbreviations for radical polymerization initiator>
V-50: 2,2'-azobis(2-amidinopropane)dihydrochloride
VA-057: 2,2'-azobis[N-(2-carboxyethyl)-2-methylpropioneamidine]tetrahydrate
PPS: potassium persulfate As is clear from Table 1, the methods of Examples 1 to 5 reduce the amount of the petroleum hydrocarbon dispersion medium released to the outside of the system, thereby lessening adverse effects on the environment. The methods of Examples 1 to 5 made it possible to obtain a water-absorbent resin having a high water-retention capacity and water-absorption capacity under a load, and a low content of water soluble component.

In contrast, in Comparative Examples, when the amount of water-soluble azo initiator for radical polymerization was small (i.e., Comparative Example 1), the reversed-phase suspension polymerization became unstable and the polymer of water-soluble ethylenic unsaturated monomer aggregated. When the amount of the water-soluble azo initiator for radical polymerization was large (i.e., Comparative Example 2), although a water-absorbent resin exhibiting high performance in various properties was obtained, the amount of the petroleum hydrocarbon dispersion medium released to the outside of the system was undesirably large. Furthermore, when the amount of the hypophosphorous compound was small (i.e., Comparative Example 3), the resulting water-absorbent resin had a low water-absorption capacity under a load, and when the amount of the hypophosphorous compound was large (i.e., Comparative Example 4), a water-absorbent resin having a high content of water soluble component was obtained. When a persulfate, instead of a water-soluble azo initiator for radical polymerization, was used as the radical polymerization (i.e., Comparative Example 5), a water-absorbent resin having a low water-absorption capacity under a load was obtained.

EXPLANATION OF NUMERICAL SYMBOLS

X Measuring device
1 Burette section
10 Burette
11 Air introduction tube
12 Cock
13 Cock
14 Rubber plug
2 Tube
3 Measuring board
4 Measuring section
40 Cylinder
41 Nylon mesh
42 Weight
5 Water-absorbent resin

The invention claimed is:
1. A method for producing a water-absorbent resin comprising:
subjecting at least one water-soluble ethylenic unsaturated monomer to reversed-phase suspension polymerization in a petroleum hydrocarbon dispersion medium,
the reversed-phase suspension polymerization being conducted using 0.00005 to 0.00016 mol of water-soluble azo initiator for radical polymerization per mol of the water-soluble ethylenic unsaturated monomer to be used in the presence of 0.000015 to 0.00015 mol of hypophosphorous compound per mol of the water-soluble ethylenic unsaturated monomer to be used.

2. The method for producing a water-absorbent resin according to claim 1, wherein the water-soluble azo initiator for radical polymerization is at least one member selected from the group consisting of 2,2'-azobis(2-amidinopropane) dihydrochloride, 2,2'-azobis {2-[1-(2-hydroxyethyl)-2-imidazolin-2-yl]propane}dihydrochloride, and 2,2'-azobis[N-(2-carboxyethyl)-2-methylpropioneamidine]tetrahydrate.

3. The method for producing a water-absorbent resin according to claim 1, wherein the hypophosphorous compound is at least one member selected from the group consisting of hypophosphorous acid and sodium hypophosphite.

4. The method for producing a water-absorbent resin according to claim 1, wherein the water-soluble ethylenic unsaturated monomer is at least one member selected from the group consisting of (meth)acrylic acid and salts thereof.

5. The method for producing a water-absorbent resin according to claim 1, wherein the reversed-phase suspension polymerization is conducted in two or more steps.

6. The method for producing a water-absorbent resin according to claim 1, wherein post-crosslinking is conducted by adding a cross-linking agent after the completion of the reversed-phase suspension polymerization of the water-soluble ethylenic unsaturated monomer.

7. A water-absorbent resin produced by the method of claim 1.

* * * * *